United States Patent

Commandeur et al.

Patent Number: 4,523,044
Date of Patent: Jun. 11, 1985

[54] COMPOSITIONS OF POLYARYLALKANE OLIGOMERS AND PROCESS FOR THEIR MANUFACTURE

[75] Inventors: Raymond Commandeur, Vizille; Bernard Gurtner, Grenoble, both of France

[73] Assignee: Atochem, Courbevoie, France

[21] Appl. No.: 650,765

[22] Filed: Sep. 13, 1984

[30] Foreign Application Priority Data

Sep. 23, 1983 [FR] France .................. 83 15127

[51] Int. Cl.³ ........................... C07C 1/16; C07C 2/02
[52] U.S. Cl. ......................................... 585/11; 585/19; 585/25; 585/320; 585/326; 585/469
[58] Field of Search ................. 585/11, 19, 25, 320, 585/426, 469

[56] References Cited

U.S. PATENT DOCUMENTS 2,377,433  6/1945  Lieber .................................... 585/19
2,850,545  9/1958  Fetterly et al. ...................... 585/426
4,251,675  2/1981  Enqel ................................... 585/469

Primary Examiner—Curtis R. Davis
Attorney, Agent, or Firm—Sigalos & Levine

[57] ABSTRACT

Polyarylalkane oligomer compositions comprising a mixture of two oligomers A and B, wherein oligomer A is a mixture of isomers of formula:

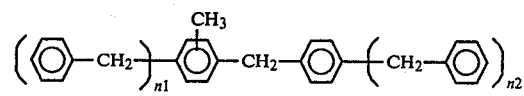

with $n1$ and $n2 = 0$, 1 and 2, given that $n1 + n2 \leq 3$; and oligomer B is a mixture of isomers of formula:

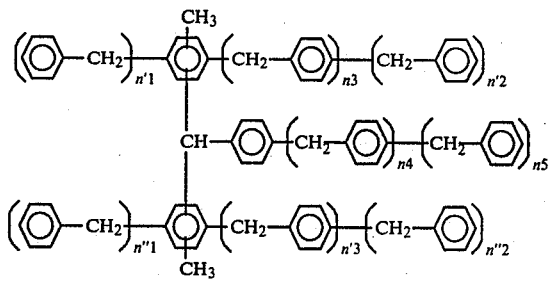

with $n'1$, $n''1$ and $n4 = 0$, 1 and 2, $n'2$, $n''2$, $n3$, $n'3$ and $n5 = 0$ and 1, given that $n'1 + n''1 + n'2 + n''2 + n3 + n'3 + n4 + n5 \leq 2$.

The invention also comprises the process for the preparation of said oligomer compositions by the action of a halide or inorganic acid on a product of free-radical chlorination of toluene.

8 Claims, No Drawings

COMPOSITIONS OF POLYARYLALKANE OLIGOMERS AND PROCESS FOR THEIR MANUFACTURE

BACKGROUND OF THE INVENTION

The present invention relates to novel compositions of polyarylalkane oligomers, and the process for manufacturing them.

These compositions of polyarylalkane oligomers consist of the mixture of two oligomers A and B. Oligomer A is a mixture of isomers of formula:

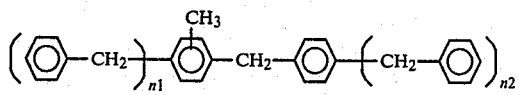

with n1 and n2=0, 1 and 2, given that n1+n2 ≦3; and oligomer B is a mixture of isomers of formula:

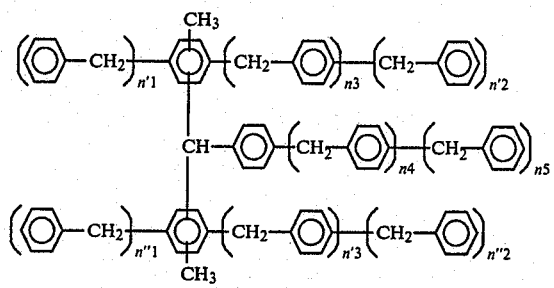

with n'1, n"1 and n4=0, 1 and 2, n'2, n"2, n3, n'3 and n5=0 and 1, given that n'1+n"1+n'2+n"2+n3+n'3+n4+n5≦2.

This mixture of polyarylalkane oligomers, composed on the one hand of benzyltoluene, dibenzyltoluene and higher homologues, and on the other hand of ditolylphenylmethane and higher homologues, can have the same applications and advantages as monobenzyltoluenes but without possessing their drawbacks. For example, pure monobenzyltoluene is useful as a dielectric for condensers, but has the drawback of crystallizing at −20° C. after supercooling which can be of long duration, which makes it unusable in cold countries. In the same application, dibenzyltoluene does not have this drawback, but its viscosity at low temperatures remains too great to make it usable. The oligomer compositions according to the invention not only have a viscosity which is always compatible with the application envisaged, but moreover they are obtained without sophisticated manufacturing processes or separation processes followed by recombination.

The disadvantages of mono- and dibenzyltoluene have been known for a long time, and numerous replacement mixtures have been proposed starting from polyarylalkane oligomers. Presently, however, it has been difficult to reconcile the quality of the properties of the oligomer products obtained with a commercially feasible method of manufacture.

Thus, in the German Offenlegungsschrift No. 3,127,905, a synthesis process is described which involves the condensation between formaldehyde and aromatic compounds, but this reaction has a poor yield by weight and leads to secondary reactions in the case of the oligomers. In fact, four starting materials are used, namely benzene, toluene, formaldehyde, and sulphuric acid. Besides oligomers of type A, formed by reaction of benzene, toluene and formaldehyde, oligomers of the diphenylmethane type are formed by reaction of benzene and formaldehyde, and of the ditolylmethane type by reaction of toluene and formaldehyde.

Finally, in Japanese Pat. No. 55-5689, the use of the following isomers as dielectric fluids is mentioned:
2,4-dibenzyltoluene
2,6-dibenzyltoluene
o-benzyltoluene
p-benzyltoluene
either separately or mixed. Apart from the fact that the synthesis of these isomers requires specific reactions, for example p-benzyltoluene starting from p-methylbenzyl chloride and benzene, or costly separations, it is still necessary subsequently to mix these isomers, which is economically disadvantageous.

Further, the use of benzyl chloride as a starting material for condensation, and its storage present some drawbacks on account of the high reactivity of benzyl chloride, which also explains its high price in comparison with other chlorinated aromatic derivatives.

Thus, products presently sought for dielectric applications, such as monobenzyltoluene or dibenzyltoluene, have only been successfully obtained utilizing syntheses of low selectivity.

SUMMARY OF THE INVENTION

The present invention overcomes the problems of the prior art.

Briefly the invention provides a polyarylalkane oligomer composition comprising a mixture of two oligomers A and B wherein oligomer A is a mixture of isomers of formula:

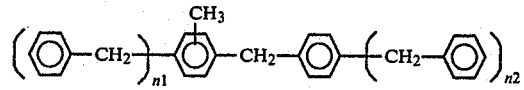

with n1 and n2=0, 1 and 2, given that n1+n2≦3; and oligomer B is a mixture of isomers of formula:

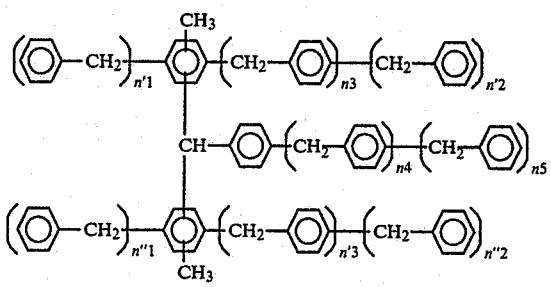

with n'1, n"1 and n4=0, 1 and 2, n'2, n"2, n3, n'3 and n5=0 and 1, given that n'1+n"1+n'2+n"2+n3+n'3+n4+n5≦2.

Further, the invention relates to the process for the manufacture of such compositions comprising reacting chlorine with toluene by free-radical reaction in the presence of a free-radical generator and subjecting this reaction product to the action of an inorganic halide or inorganic acid at a temperature and for a time sufficient to form the oligomer composition.

DETAILED DESCRIPTION

The compositions of polyarylalkane oligomers according to the invention are obtained by carrying out a synthesis process which does not involve the reaction of benzylchloride with an aromatic compound, but simply the reaction of chlorine with toluene.

The free-radical chlorination of toluene is usually carried out at a temperature between 50° and 110° C., preferably between 70° and 100° C. It is preferably performed in such a way that only 10 to 30% of the toluene present, expressed as a molar percentage, is converted to the corresponding chlorinated derivative. As a free-radical generator, either photochemical initiation or a chemical initiator can be employed. Chemical initiators may include azo compounds such as azodiisobutyronitrile or azodivaleronitrile and lauroyl peroxide. The quantity of chemical initiator used is generally between 0.05 and 3% by weight relative to the toluene present, and preferably between 0.1 and 1.5%.

The reaction medium obtained during the preceding stage is then subjected to the action of an inorganic halide or inorganic acid. This second state reaction takes place in practice at a temperature between 30° and 100° C., and preferably between 50° and 100° C. Inorganic halides that can be used include ferric chloride, antimony trichloride, titanium tetrachloride, or aluminum chloride, at concentrations by weight relative to the reaction medium usually between 50 ppm and 1%, and preferably between 100 ppm and 0.5%. Inorganic acids can also be used, for example, sulphuric acid at a concentration between 70 and 95% by weight. It is also possible to use zeolites or certain inorganic oxides. A variant of the process at the second state consists in running the reaction mixture from the first phase into a small quantity of toluene, or of toluene and the mixture of oligomers according to the invention, containing the inorganic halide or acid in solution or dispersion. This variant is particularly advantageous for putting such a process into continuous operation, since it is very clear that this synthesis can be carried out both as a batch process and continuously.

After distilling off the excess toluene, it is recommended that the inorganic halide or acid should be removed by any known technique, such as washing with water, neutralization, and drying.

According to the process described, the mixture of polyarylalkane oligomers is usually obtained directly in the following proportions by weight:

Compound A as a mixture of isomers:
$n1+n2=0$, between 56 and 90%,
$n1+n2=1$, between 7 and 28%,
$n1+n2=2$, between 1.5 and 8%,
$n1+n2=3$, between 0.1 and 1%.

Compound B as a mixture of isomers:
$n'1+n''1+n'2+n''2+n3+n'3+n4+n5=0$ between 1.1 and 5%,
$n'1+n''1+n'2+n''2+n'3+n4+n5=1$ between 0.25 and 1.5%,
$n'1+n''1+n'2+n''2+n3+n'3+n4+n5=2$ between 0.05 and 0.5%.

Depending on the application for which the mixture of polyarylalkane oligomers is to be used, it can be advantageous to carry out a flash-evaporation of this mixture to remove the traces of impurities which come from either the starting materials or the process. In any case, their content does not exceed 1 to 2% by weight. Among the apparatus which can be used, a thin film evaporator will be preferred. It should be pointed out however that, at the industrial level, the technical possibilities of such apparatus as regards the behavior in vacuum do not always permit the totality of the mixture of polyarylalkane oligomers to be recovered. These evaporated products nevertheless form an integral part of the invention, as is notably the case of the isomers of compound A where $n1+n2=3$ and of compound B where $n'1+n''1+n'2+n''2+n3+n'3+n4+n5=2$.

The mixtures of oligomers are obtained, according to the process described, in yields which can, under the best conditions, even reach 98% by weight, expressed relative to the toluene reacted.

The invention will be further illustrated in conjunction with the following examples, which are set forth for purposes of illustration only and not by way of limitation. The composition of the reaction media is defined:

by distillation under a vacuum of 2 mm of Hg (267 Pa)
A: $n1+n2=0$, boiling range=90°-130° C.
(A: $n1+n2=1$), boiling range= (B: $n'1+n''1+n'2+n''2+n3+n'3+n4+n5=0$) 130°-200° C.
(A: $n1+n2=2$), boiling range=(B: $n'1+n''1+n'2+n''2+n3+n'3+n4+n5=1$) 200°-250° C.
(A: $n1+n2=3$) distillation, (B: $n'1+n''1+n'2+n''2+n3+n'3+n4+n5 \leq 2$) residue;

and by determination of the content of compound B in each of the distillation fractions, by proton-NMR in $CDCl_3$ medium with tetramethylsilane as reference. The proton of the CH group corresponding to triphenylmethane derivatives has a chemical shift at 5.5 ppm.

EXAMPLE 1

368 g of toluene (3.8 moles) is placed in a reactor provided with stirring and equipped with a condenser, a chlorine supply tube and a PHILIPS TLADK 30 watt lamp. 71 g of chlorine gas (1 mole) is then introduced while maintaining the temperature at 80° C. for one hour. After the photochemical initiation has stopped, the reaction medium is placed in a dropping funnel, and introduced in the course of one hour into a reactor provided with stirring, and containing 0.2 mole of toluene and 60 mg of $FeCl_3$, at a temperature of 100° C. The assembly is maintained at 100° C. with stirring for a further 1 hour after the addition is complete.

After being cooled, the reaction mixture is washed with 10% strength hydrochloric acid, then with water to neutrality, and finally the excess of toluene is removed by distillation. The mixture of polyarylalkane oligomers obtained has the following composition by weight:

| PRODUCT | n1 + n2 | | | | n'1 + n''1 + n'2 + n''2 + n3 + n'3 + n4 + n5 | | |
|---------|---|---|---|---|---|---|---|
|  | 0 | 1 | 2 | 3 | 0 | 1 | 2 |
| A | 64% | 21.8% | 7.8% | 2.8% | — | — | — |
| B | — | — | — | — | 2.5% | 0.9% | 0.3% |

Regarding viscosity: at 50° C. = 6.5 cSt
20° C. = 10.5 cSt
−20° C. = 33 cSt

The yield by weight, calculated in relation to toluene reacted, is 98%.

This product, when subjected to flask evaporation at 300° C. under 2 mm of Hg (267 Pa) gives, in a 95% yield, a mixture of polyarylalkane oligomers in which the only difference from the composition given above is the absence of products corresponding to:

A where $n1+n2=3$,

B where $n'1+n''1+n'2+n''2+n3+n'3+n4+n5=2$.

EXAMPLE 2

By proceeding under the same reaction conditions as in Example 1, but with 552 g of toluene (5.8 moles) present for 71 g of chlorine (1 mole), and then with 100 mg of $FeCl_3$ and 0.2 mole of toluene present in the coupling reaction there is obtained a mixture of polyarylalkane oligomers having the following composition by weight:

| PRODUCT | $n1 + n2$ | | | | $n'1 + n''1 + n'2 + n''2 + n3 + n'3 + n'3 + n4 + n5$ | | |
|---|---|---|---|---|---|---|---|
| | 0 | 1 | 2 | 3 | 0 | 1 | 2 |
| A | 77% | 15.5% | 4.0% | 0.9% | — | — | — |
| B | — | — | — | — | 2.0% | 0.5% | 0.1% |

Viscosity: at 50° C. = 2.8 cSt
20° C. = 6.5 cSt
−30° C. = 100 cSt.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. Polyarylalkane oligomer compositions comprising a mixture of two oligomers A and B, wherein oligomer A is a mixture of isomers of formula:

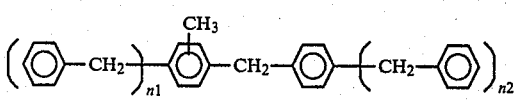

with n1 and $n2=0$, 1 and 2, given that $n1+n2\leq 3$; and oligomer B is a mixture of isomers of formula:

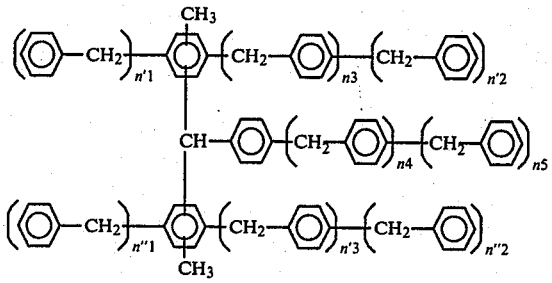

with n'1, n''1 and $n4=0$, 1 and 2, n'2, n''2, n3, n'3 and $n5=0$ and 1, given that $n'1+n''1+n'2+n''2+n3+n'3+n4+n5\leq 2$.

2. The composition of claim 1, wherein the mixture of oligomers occurs in the following proportions by weight:

compound A as a mixture of isomers:
$n1+n2=0$ between 56 and 90%;
$n1+n2=1$, between 7 and 28%;
$n1+n2=2$, between 1.5 and 8%; and
$n1+n2=3$, between 0.1 and 1%;

and compound B as a mixture of isomers:
$n'1+n''1+n'2+n''2+n3+n'3+n4+n5=0$, between 1.1 and 5%;
$n'1+n''1+n'2+n''2+n3+n'3+n4+n5=1$, between 0.25 and 1.5%; and
$n'1+n''1+n'2+n''2+n3+n'3+n4+n5=2$, between 0.05 and 0.5%.

3. The composition of claim 2, wherein the mixture of oligomers occurs in the following proportions by weight:

Compound A as a mixture of isomers:
$n1+n2=0$, between 56 and 90%;
$n1+n2=1$, between 7 and 28;
$n1+n2=2$, between 1.5 and 8%;

and compound B as a mixture of isomers:
$n'1+n''1+n'2+n''2+n3+n'3+n4+n5=0$, between 1.1 and 5%; and
$n'1+n''1+n'2+n''2+n3+n'3+n4+n5=1$, between 0.25 and 1.5%.

4. The process for the manufacture of compositions of polyarylalkane oligomers comprising, in a first stage, reacting chlorine with toluene by free-radical reaction in the presence of a free-radical generator and, in a second stage, subjecting the reaction product from said first stage to the action of an inorganic halide or inorganic acid for a time and at a temperature sufficient to form said oligomers.

5. The process of claim 4, wherein the first stage only 10 to 30%, in molar terms, of the toluene present is converted to the corresponding chlorinated derivatives.

6. The process of claim 4 or 5, wherein the free-radical chlorination of toluene is carried out at a temperature between 50° C. and 110° C., and preferably between 70° C. and 100° C.

7. The process of claim 4 or 5, wherein said second stage reaction occurs at a temperature between 30° and 110° C., and preferably between 50° and 100° C.

8. The process of claim 6 or 7, wherein a flash-evaporation is performed on the product obtained in the second stage.

* * * * *